(12) United States Patent
Romero

(10) Patent No.: US 8,574,230 B2
(45) Date of Patent: *Nov. 5, 2013

(54) OPEN VESSEL SEALING INSTRUMENT WITH PIVOT ASSEMBLY

(71) Applicant: Covidien LP, Mansfield, MA (US)

(72) Inventor: Paul R. Romero, Loveland, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/747,090

(22) Filed: Jan. 22, 2013

(65) Prior Publication Data

US 2013/0138104 A1 May 30, 2013

Related U.S. Application Data

(62) Division of application No. 12/553,509, filed on Sep. 3, 2009, now Pat. No. 8,357,159.

(51) Int. Cl.
*A61B 18/18* (2006.01)
(52) U.S. Cl.
USPC .................................. 606/51; 606/52; 606/45
(58) Field of Classification Search
USPC ...................................................... 606/45–52
See application file for complete search history.

(56) References Cited

U.S. PATENT DOCUMENTS

| D249,549 S | 9/1978 | Pike |
|---|---|---|
| D263,020 S | 2/1982 | Rau, III |
| D295,893 S | 5/1988 | Sharkany et al. |
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |

(Continued)

FOREIGN PATENT DOCUMENTS

| CN | 201299462 | 9/2009 |
|---|---|---|
| DE | 2415263 A1 | 10/1975 |

(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

(Continued)

*Primary Examiner* — Linda Dvorak
*Assistant Examiner* — Amanda Scott

(57) ABSTRACT

An open electrosurgical forceps includes a pair of first and second shaft members each having a jaw member disposed at its distal end. The jaw members are movable about a pivot assembly from an open position in spaced relation relative to one another to a closed position wherein the jaw members cooperate to grasp tissue. Each of the jaw members includes an electrically conductive sealing surface for communicating electrosurgical energy through grasped tissue. One or both of the jaw members includes a knife channel defined along its length. The pivot assembly includes a knife slot and is configured to prevent reciprocation of a cutting mechanism when the jaw members are disposed in the open position and to permit reciprocation of the cutting mechanism when the jaw members are disposed in the closed position. An actuator selectively advances the cutting mechanism from a first position to at least one subsequent position.

3 Claims, 10 Drawing Sheets

(56) References Cited

U.S. PATENT DOCUMENTS

| | | |
|---|---|---|
| D384,413 S | 9/1997 | Zlock et al. |
| H1745 H | 8/1998 | Paraschac |
| 5,810,811 A | 9/1998 | Yates et al. |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H1904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H2037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| 7,101,371 B2 | 9/2006 | Dycus et al. |
| D531,311 S | 10/2006 | Guerra et al. |
| 7,131,970 B2 | 11/2006 | Moses et al. |
| D533,274 S | 12/2006 | Visconti et al. |
| D533,942 S | 12/2006 | Kerr et al. |
| 7,150,097 B2 | 12/2006 | Sremcich et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinge |
| D541,938 S | 5/2007 | Kerr et al |
| D545,432 S | 6/2007 | Watanabe |
| D547,154 S | 7/2007 | Lee |
| 7,252,667 B2 | 8/2007 | Moses et al. |
| 7,255,697 B2 | 8/2007 | Dycus et al. |
| 7,267,677 B2 | 9/2007 | Johnson et al. |
| 7,329,256 B2 | 2/2008 | Johnson et al. |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| 7,491,201 B2 | 2/2009 | Shields et al. |
| 7,500,975 B2 | 3/2009 | Cunningham et al. |
| 7,513,898 B2 | 4/2009 | Johnson et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| 7,887,536 B2 | 2/2011 | Johnson et al. |
| 8,016,827 B2 | 9/2011 | Chojin |
| D649,249 S | 11/2011 | Guerra |
| D649,643 S | 11/2011 | Allen, IV et al. |
| 8,112,871 B2 | 2/2012 | Brandt et al. |
| 8,114,122 B2 | 2/2012 | Nau, Jr. |
| 8,133,254 B2 | 3/2012 | Dumbauld et al. |
| 8,142,473 B2 | 3/2012 | Cunningham |
| 8,162,965 B2 | 4/2012 | Reschke et al. |
| 8,162,973 B2 | 4/2012 | Cunningham |
| D661,394 S | 6/2012 | Romero et al. |
| 8,197,479 B2 | 6/2012 | Olson et al. |
| 8,226,650 B2 | 7/2012 | Kerr |
| 8,251,994 B2 | 8/2012 | McKenna et al. |
| 8,257,387 B2 | 9/2012 | Cunningham |
| 8,266,783 B2 | 9/2012 | Brandt et al. |
| 8,277,446 B2 | 10/2012 | Heard |
| 8,282,634 B2 | 10/2012 | Cunningham et al. |
| 8,287,536 B2 | 10/2012 | Mueller et al. |
| 8,292,886 B2 | 10/2012 | Kerr et al. |
| 8,303,582 B2 | 11/2012 | Cunningham |
| 8,317,787 B2 | 11/2012 | Hanna |
| 8,323,310 B2 | 12/2012 | Kingsley |
| 8,328,803 B2 | 12/2012 | Regadas |
| 8,343,150 B2 | 1/2013 | Artale |
| 8,343,151 B2 | 1/2013 | Siebrecht et al. |
| 8,357,159 B2 | 1/2013 | Romero |
| 8,388,647 B2 | 3/2013 | Nau, Jr. et al. |
| 8,430,876 B2 | 4/2013 | Kappus et al. |
| 8,439,911 B2 | 5/2013 | Mueller |
| 2002/0107517 A1 | 8/2002 | Witt et al. |
| 2002/0111624 A1 | 8/2002 | Witt et al. |
| 2003/0018331 A1 | 1/2003 | Dycus et al. |
| 2003/0229344 A1 | 12/2003 | Dycus et al. |
| 2005/0107784 A1 | 5/2005 | Moses et al. |
| 2005/0154387 A1 | 7/2005 | Moses et al. |
| 2006/0074417 A1 | 4/2006 | Cunningham et al. |
| 2009/0149854 A1 | 6/2009 | Cunningham et al. |
| 2010/0016857 A1 | 1/2010 | McKenna et al. |
| 2010/0023009 A1 | 1/2010 | Moses et al. |
| 2010/0042143 A1 | 2/2010 | Cunningham |
| 2010/0049187 A1 | 2/2010 | Carlton et al. |
| 2010/0057081 A1 | 3/2010 | Hanna |
| 2010/0057082 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |
| 2010/0094287 A1 | 4/2010 | Cunningham et al. |
| 2010/0100122 A1 | 4/2010 | Hinton |
| 2010/0179545 A1 | 7/2010 | Twomey et al. |
| 2010/0179546 A1 | 7/2010 | Cunningham |
| 2010/0249769 A1 | 9/2010 | Nau, Jr. et al. |
| 2010/0280511 A1 | 11/2010 | Rachlin et al. |
| 2011/0034918 A1 | 2/2011 | Reschke |
| 2011/0046623 A1 | 2/2011 | Reschke |
| 2011/0054468 A1 | 3/2011 | Dycus |
| 2011/0054471 A1 | 3/2011 | Gerhardt et al. |
| 2011/0060334 A1 | 3/2011 | Brandt et al. |
| 2011/0060335 A1 | 3/2011 | Harper et al. |
| 2011/0071523 A1 | 3/2011 | Dickhans |
| 2011/0077648 A1 | 3/2011 | Lee et al. |
| 2011/0082494 A1 | 4/2011 | Kerr et al. |
| 2013/0103030 A1 | 4/2013 | Garrison |
| 2013/0103031 A1 | 4/2013 | Garrison |
| 2013/0103035 A1 | 4/2013 | Horner et al. |
| 2013/0103041 A1 | 4/2013 | Regadas |
| 2013/0116690 A1 | 5/2013 | Unger |
| 2013/0123780 A1 | 5/2013 | McKenna et al. |
| 2013/0123837 A1 | 5/2013 | Roy et al. |
| 2013/0131672 A1 | 5/2013 | Romero |
| 2013/0138101 A1 | 5/2013 | Kerr |
| 2013/0138102 A1 | 5/2013 | Twomey et al. |
| 2013/0138104 A1 | 5/2013 | Romero |
| 2013/0138129 A1 | 5/2013 | Garrison et al. |
| 2013/0144284 A1 | 6/2013 | Behnke, II et al. |
| 2013/0150842 A1 | 6/2013 | Nau, Jr. et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |

(56) References Cited

FOREIGN PATENT DOCUMENTS

| | | |
|---|---|---|
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1 159 926 A2 | 12/2001 |
| EP | 1330991 | 7/2003 |
| EP | 1486177 | 6/2004 |
| EP | 1532932 | 5/2005 |
| EP | 1609430 | 12/2005 |
| EP | 1645240 | 4/2006 |
| EP | 0875209 B1 | 5/2006 |
| EP | 1707143 | 10/2006 |
| JP | 61-501068 | 9/1984 |
| JP | 10-24051 A | 1/1989 |
| JP | 11-47150 A | 6/1989 |
| JP | 6-502328 | 3/1992 |
| JP | 5-5106 | 1/1993 |
| JP | 05-40112 | 2/1993 |
| JP | 0006030945 A | 2/1994 |
| JP | 6-285078 A | 10/1994 |
| JP | 06343644 A | 12/1994 |
| JP | 07265328 A | 10/1995 |
| JP | 08056955 A | 3/1996 |
| JP | 08252263 A | 10/1996 |
| JP | 8-289895 A | 11/1996 |
| JP | 8-317934 A | 12/1996 |
| JP | 8-317936 A | 12/1996 |
| JP | 09000538 A | 1/1997 |
| JP | 09010223 A | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-13652 A | 5/2002 |
| JP | 2002-528166 A | 9/2002 |
| JP | 2003-116871 A | 4/2003 |
| JP | 2003245285 A | 9/2003 |
| JP | 2004-517668 A | 6/2004 |
| JP | 2004-528869 A | 9/2004 |
| JP | 2005-152663 A | 6/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | WO-0036986 A1 | 6/2000 |
| WO | WO-0059392 A1 | 10/2000 |
| WO | WO-0115614 A1 | 3/2001 |
| WO | WO-0154604 A1 | 8/2001 |
| WO | WO-02045589 A3 | 9/2002 |
| WO | WO-2005/110264 A2 | 11/2005 |
| WO | WO-2006/021269 A1 | 3/2006 |
| WO | WO-2008/040483 A1 | 4/2008 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000.

Johnson et al. "Evaluation of a Bipolar Electrothermal Vessel Sealing Device in Hemorrhoidectomy" Sales/Product Literature; Jan. 2004.

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Carus et al., "Initial Experience With the LigaSure Vessel Sealing System in Abdominal Surgery" Innovations That Work, Jun. 2002.

Heniford et al. "Initial Research and Clinical Results with an Electrothermal Bipolar Vessel Sealer" Oct. 1999.

Heniford et al. "Initial Results with an Electrothermal Bipolar Vessel Sealer" Surgical Endoscopy (2000) 15:799-801.

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001.

Bergdahl et al. "Studies on Coagulation and the Development of an Automatic Computerized Bipolar Coagulator" J.Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

(56) References Cited

OTHER PUBLICATIONS

Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics IGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 20, 2000, Thomas P. Ryan.
U.S. Appl. No. 12/336,970, filed Dec. 17, 2008, Paul R. Sremcich.
U.S. Appl. No. 13/344,729, filed Jan. 6, 2012, James D. Allen, IV.
U.S. Appl. No. 13/355,829, filed Jan. 23, 2012, John R. Twomey.
U.S. Appl. No. 13/357,979, filed Jan. 25, 2012, David M. Garrison.
U.S. Appl. No. 13/358,136, filed Jan. 25, 2012, James D. Allen, IV.
U.S. Appl. No. 13/360,925, filed Jan. 30, 2012, James H. Orszulak.
U.S. Appl. No. 13/400,290, filed Feb. 20, 2012, Eric R. Larson.
U.S. Appl. No. 13/404,435, filed Feb. 24, 2012, Kim V. Brandt.
U.S. Appl. No. 13/404,476, filed Feb. 24, 2012, Kim V. Brandt.
U.S. Appl. No. 13/412,879, filed Mar. 6, 2012, David M. Garrison.
U.S. Appl. No. 13/412,897, filed Mar. 6, 2012, Joanna Ackley.
U.S. Appl. No. 13/421,373, filed Mar. 15, 2012, John R. Twomey.
U.S. Appl. No. 13/430,325, filed Mar. 26, 2012, William H. Nau, Jr.
U.S. Appl. No. 13/433,924, filed Mar. 29, 2012, Keir Hart.
U.S. Appl. No. 13/448,577, filed Apr. 17, 2012, David M. Garrison.
U.S. Appl. No. 13/460,455, filed Apr. 30, 2012, Luke Waaler.
U.S. Appl. No. 13/461,335, filed May 1, 2012, James D. Allen, IV.
U.S. Appl. No. 13/461,378, filed May 1, 2012, James D. Allen, IV.
U.S. Appl. No. 13/461,397, filed May 1, 2012, James R. Unger.
U.S. Appl. No. 13/461,410, filed May 1, 2012, James R. Twomey.
U.S. Appl. No. 13/466,274, filed May 8, 2012, Stephen M. Kendrick.
U.S. Appl. No. 13/467,767, filed May 9, 2012, Duane E. Kerr.
U.S. Appl. No. 13/470,775, filed May 14, 2012, James D. Allen, IV.
U.S. Appl. No. 13/482,589, filed May 29, 2012, Eric R. Larson.
U.S. Appl. No. 13/483,733, filed May 30, 2012, Dennis W. Butcher.
U.S. Appl. No. 13/537,517, filed Jun. 29, 2012, David N. Heard.
U.S. Appl. No. 13/537,577, filed Jun. 29, 2012, Tony Moua.
U.S. Appl. No. 13/708,335, filed Dec. 7, 2012, Dumbauld.
U.S. Appl. No. 13/731,674, filed Dec. 31, 2012, Siebrecht.
U.S. Appl. No. 13/741,550, filed Jan. 15, 2013, Deborski.
U.S. Appl. No. 13/799,173, filed Mar. 13, 2013, Larson.
U.S. Appl. No. 13/803,636, filed Mar. 14, 2013, Kerr.
U.S. Appl. No. 13/803,762, filed Mar. 14, 2013, Kerr.
U.S. Appl. No. 13/803,884, filed Mar. 14, 2013, Kerr.
U.S. Appl. No. 13/804,010, filed Mar. 14, 2013, Kerr.
U.S. Appl. No. 13/833,823, filed Mar. 15, 2013, Garrison.
U.S. Appl. No. 13/834,703, filed Mar. 15, 2013, Garrison.
U.S. Appl. No. 13/835,004, filed Mar. 15, 2013, Twomey.
U.S. Appl. No. 13/838,945, filed Mar. 15, 2013, Stoddard.
U.S. Appl. No. 13/853,259, filed Mar. 29, 2013, Garrison.
U.S. Appl. No. 13/853,273, filed Mar. 29, 2013, Kerr.
U.S. Appl. No. 13/853,339, filed Mar. 29, 2013, Reschke.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.

OPEN VESSEL SEALING INSTRUMENT WITH PIVOT ASSEMBLY

CROSS-REFERENCE TO RELATED APPLICATIONS

This application is a divisional of claims the benefit to U.S. patent application Ser. No. 12/553,509, filed Sep. 3, 2009, entitled "OPEN VESSEL SEALING INSTRUMENT WITH PIVOT ASSEMBLY," the content of which is hereby incorporated by reference.

BACKGROUND

1. Technical Field

The present disclosure relates to forceps used for open surgical procedures. More particularly, the present disclosure relates to an open forceps that applies a combination of mechanical clamping pressure and electrosurgical energy to seal tissue and a knife that is selectively advanceable to sever tissue along the tissue seal.

2. Background of Related Art

A forceps is a plier-like instrument that relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize both mechanical clamping action and electrical energy to effect hemostasis by heating tissue and blood vessels to coagulate and/or cauterize tissue.

Certain surgical procedures require more than simply cauterizing tissue and rely on the unique combination of clamping pressure, precise electrosurgical energy control and gap distance (i.e., distance between opposing jaw members when closed about tissue) to "seal" tissue, vessels and certain vascular bundles.

Vessel sealing or tissue sealing is a recently-developed technology that utilizes a unique combination of radiofrequency energy, pressure and gap control to effectively seal or fuse tissue between two opposing jaw members or sealing plates. Vessel or tissue sealing is more than "cauterization" which involves the use of heat to destroy tissue (also called "diathermy" or "electrodiathermy"). Vessel sealing is also more than "coagulation" which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

In order to effectively "seal" tissue or vessels, two predominant mechanical parameters should be accurately controlled: 1) the pressure or closure force applied to the vessel or tissue; and 2) the gap distance between the conductive tissue contacting surfaces (electrodes). As can be appreciated, both of these parameters are affected by the thickness of the tissue being sealed. Accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal. It has been determined that a good seal for certain tissues is optimum between about 0.001 inches and about 0.006 inches.

With respect to smaller vessels or tissue, the pressure applied becomes less relevant and the gap distance between the electrically conductive surfaces becomes more significant for effective sealing. In other words, the chances of the two electrically conductive surfaces touching during activation increases as the tissue thickness and the vessels become smaller.

Commonly owned, U.S. Pat. No. 6,511,480, PCT Patent Application Nos. PCT/US01/11420 and PCT/US01/11218, U.S. patent application Ser. Nos. 10/116,824, 10/284,562 and 10/299,650 all describe various open surgical forceps that seal tissue and vessels.

Typically, and particularly with respect to open electrosurgical procedures, once a vessel is sealed, the surgeon has to remove the sealing instrument from the operative site, substitute a new instrument and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue sealing line.

Many endoscopic vessel sealing instruments have been designed that incorporate a knife or blade member that effectively severs the tissue after forming a tissue seal. For example, commonly-owned U.S. application Ser. Nos. 10/116,944 and 10/179,863 describe one such endoscopic instrument that effectively seals and cuts tissue along the tissue seal. Other instruments include blade members or shearing members that simply cut tissue in a mechanical and/or electromechanical manner and are relatively ineffective for vessel sealing purposes.

There exists a need to develop an open electrosurgical forceps that is simple, reliable and inexpensive to manufacture and that effectively seals tissue and vessels and that allows a surgeon to utilize the same instrument to effectively sever the tissue along the newly formed tissue seal.

SUMMARY

According to an embodiment of the present disclosure, an open electrosurgical forceps includes a pair of first and second shaft members each having a jaw member disposed at its distal end. The jaw members are movable about a pivot assembly from an open position in spaced relation relative to one another to a closed position wherein the jaw members cooperate to grasp tissue. Each of the jaw members includes an electrically conductive sealing surface for communicating electrosurgical energy through grasped tissue. One or both of the jaw members includes a knife channel defined along its length. The pivot assembly includes a knife slot and is configured to prevent reciprocation of a cutting mechanism when the jaw members are disposed in the open position and to permit reciprocation of the cutting mechanism when the jaw members are disposed in the closed position. An actuator selectively advances the cutting mechanism from a first position to at least one subsequent position.

According to another embodiment of the present disclosure, an open electrosurgical forceps includes a pair of first and second shaft members each having a jaw member disposed at its distal end. The jaw members are movable about a pivot assembly from an open position in spaced relation relative to one another to a closed position wherein the jaw members cooperate to grasp tissue. The pivot assembly includes a pair of insulative shoulders having a first end defining a cap and a second end operably coupled to opposing sides of an insulative hub. One of the jaw members is configured to rotate about one of the insulative shoulders. Each of the jaw members includes an electrically conductive sealing surface for communicating electrosurgical energy through tissue grasped therebetween to effect a tissue seal. The insulative hub includes a knife slot defined therein. The pivot assembly is configured to prevent reciprocation of a cutting mechanism when the jaw members are disposed in the open position and to permit reciprocation of the cutting mechanism therethrough when the jaw members are disposed in the closed position.

According to another embodiment of the present disclosure, a pivot assembly for use with an open electrosurgical forceps for sealing tissue includes a pair of insulative shoulders having a first end defining a cap and a second end operably coupled to opposing sides of an insulative hub. The insulative hub includes a knife slot defined therein. The insulative hub is configured to prevent reciprocation of a cutting mechanism through the knife slot in a first configuration and to permit reciprocation of the cutting mechanism through the knife slot in a second configuration. The knife slot is configured to align with a knife channel when the forceps is disposed in a first configuration to permit advancement of the cutting mechanism from a retracted position proximal to the pivot assembly to an advanced position through the pivot assembly and into tissue grasped by the forceps. The knife slot is configured to misalign with the knife channel when the forceps is disposed in a second configuration to prevent advancement of the cutting mechanism from the retracted position to the advanced position.

BRIEF DESCRIPTION OF THE DRAWINGS

Various embodiments of the subject instrument are described herein with reference to the drawings wherein.

DETAILED DESCRIPTION

Figure 1:
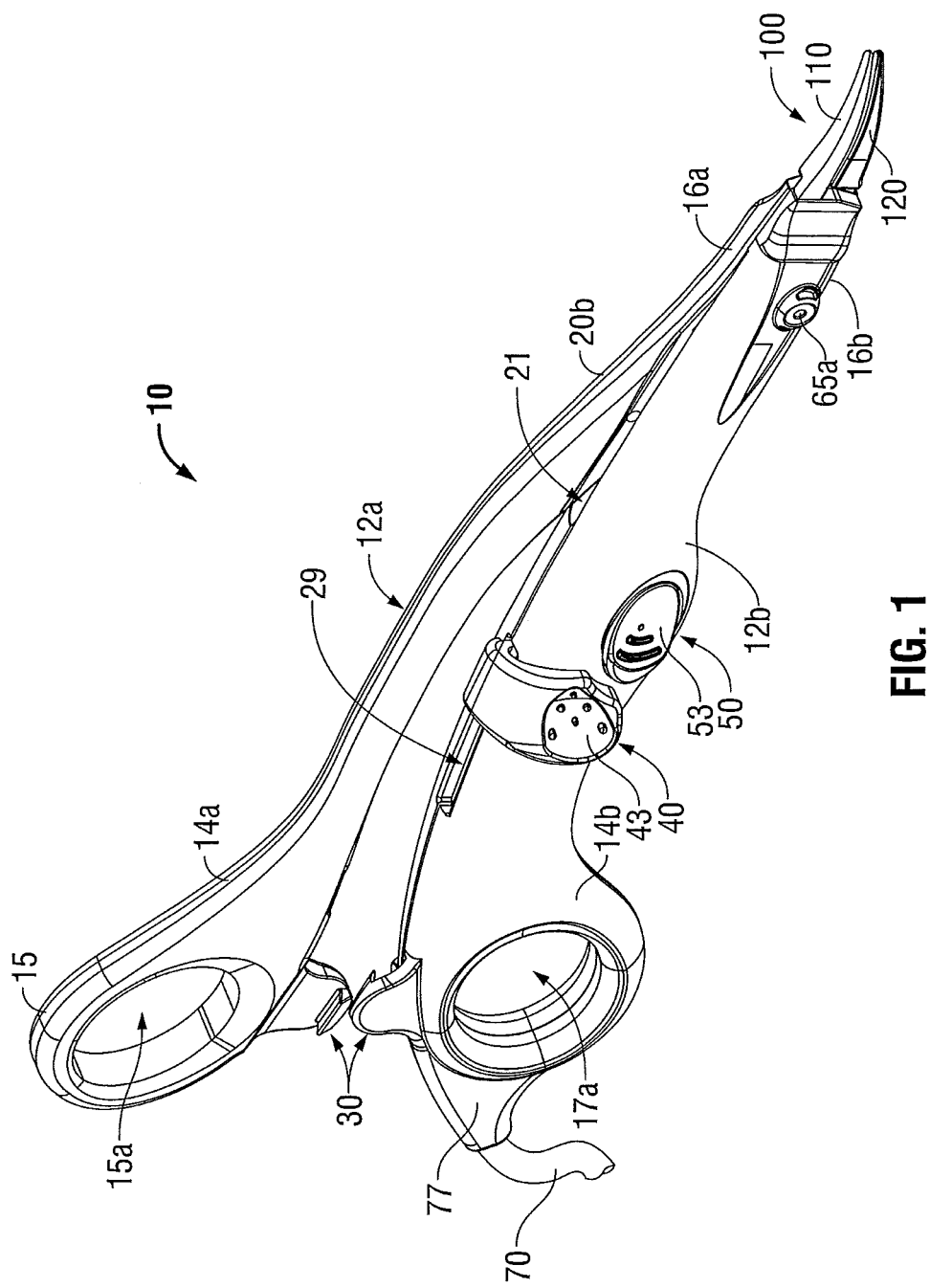
FIG. 1 is a left, front perspective view of an open forceps with a cutting mechanism according to an embodiment of the present disclosure.

Referring now to FIG. 1, a forceps 10 for use with open surgical procedures includes elongated shaft portions 12a and 12b each having a proximal end 14a, 14b and a distal end 16a and 16b, respectively. In the drawings and in the descriptions that follow, the term "proximal", as is traditional, will refer to the end of the forceps 10 that is closer to the user, while the term "distal" will refer to the end that is further from the user.

The forceps 10 includes an end effector assembly 100 that attaches to the distal ends 16a and 16b of shafts 12a and 12b, respectively. As explained in more detail below, the end effector assembly 100 includes pair of opposing jaw members 110 and 120 that are pivotably connected about a pivot assembly 65 (See FIGS. 5A-5D) and that are movable relative to one another to grasp tissue.

Each shaft 12a and 12b includes a handle 15 and 17, respectively, disposed at the proximal end 14a and 14b thereof that each define a finger hole 15a and 17a, respectively, therethrough for receiving a finger of the user. Finger holes 15a and 17a facilitate movement of the shafts 12a and 12b relative to one another that, in turn, pivot the jaw members 110 and 120 from an open position wherein the jaw members 110 and 120 are disposed in spaced relation relative to one another to a clamping or closed position wherein the jaw members 110 and 120 cooperate to grasp tissue therebetween. As shown in FIG. 1, a ratchet 30 mechanism is disposed at the proximal ends 14a, 14b of shafts 12a, 12b, respectively, for selectively locking the jaw members 110 and 120 relative to one another in at least one position during pivoting.

Figure 4:
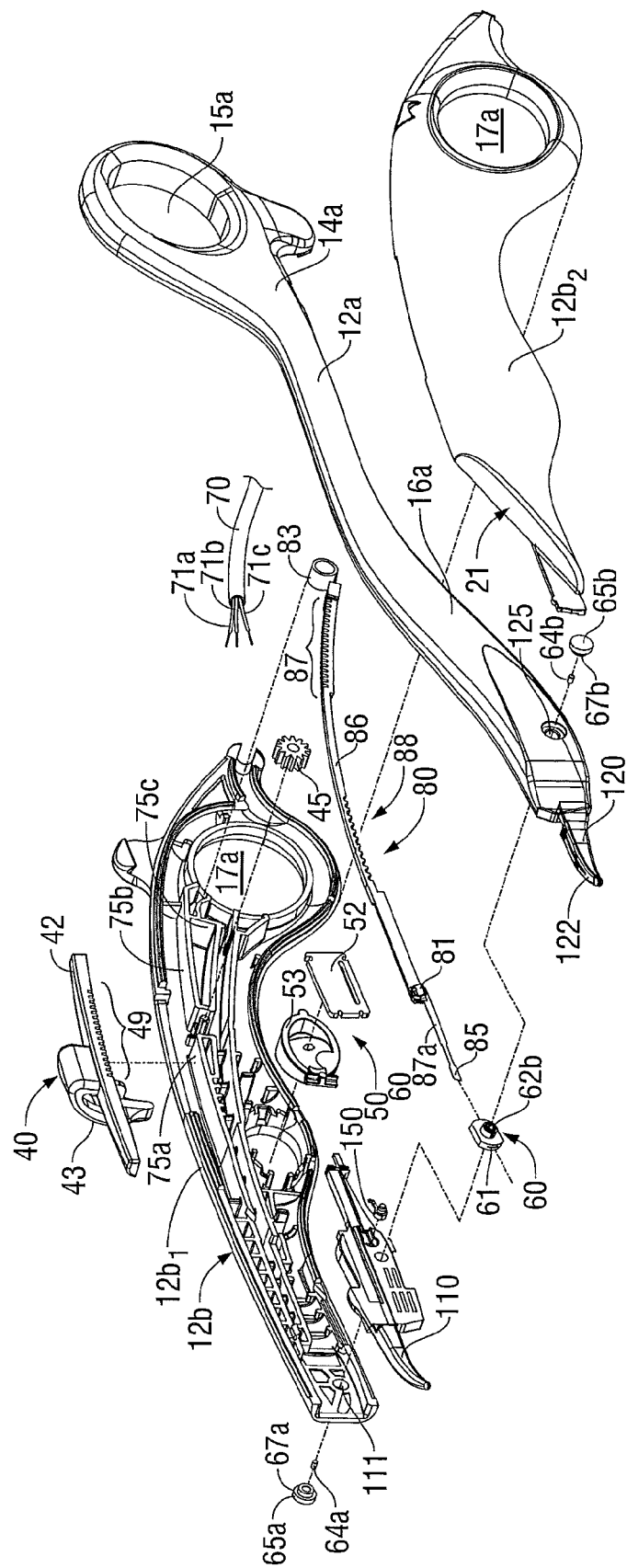
FIG. 4 is a perspective view of the forceps of FIG. 1 with parts separated.

As best seen in FIG. 4, shaft 12b is constructed from two components, namely, $12b_1$ and $12b_2$, which matingly engage one another about the distal end 16a of shaft 12a to form shaft 12b. In some embodiments, the two component halves $12b_1$ and $12b_2$ may be ultrasonically-welded together at a plurality of different weld points or the component halves $12b_1$ and $12b_2$ may be mechanically engaged in any other known fashion, snap-fit, glued, screwed, etc. After component halves $12b_1$ and $12b_2$ are welded together to form shaft 12b, shaft 12a is secured about pivot assembly 65 and positioned within a cut-out or relief 21 defined within shaft portion $12b_2$ such that shaft 12a is movable relative to shaft 12b. More particularly, when the user moves the shaft 12a relative to shaft 12b to close or open the jaw members 110 and 120, the distal portion of shaft 12a moves within cutout 21 formed within portion $12b_2$.

Jaw member 110 includes an electrically conductive sealing surface 112 that conducts electrosurgical energy of a first potential to tissue. Likewise, jaw member 120 includes an electrically conductive sealing surface 122 that conducts electrosurgical energy of a second potential to tissue.

As best illustrated in FIG. 1, one of the shafts, e.g., 12b, includes a proximal shaft connector 77 that is designed to connect the forceps 10 to a source of electrosurgical energy, such as an electrosurgical generator (not shown). The proximal shaft connector 77 electromechanically engages an electrosurgical cable 70 so that a user may selectively apply electrosurgical energy as needed. Alternatively, the cable 70 may be feed directly into shaft 12b (or 12a).

The distal end of the cable 70 may connect to a handswitch 50 to permit the user to selectively apply electrosurgical energy as needed to seal tissue grasped between jaw members 110 and 120. More particularly, the interior of cable 70 houses leads 71a, 71b and 71c that upon activation of the handswitch 50 conduct different electrical potentials from the electrosurgical generator to each of the jaw members 110 and 120 (See FIGS. 2 and 3). The electrosurgical cable 70 is fed into the bottom of shaft 12b and is held securely therein by one or more mechanical interfaces (not shown). Lead 71c extends directly from cable 70 and connects to jaw member 120 at connection 117 to conduct the second electrical potential thereto. Leads 71a and 71b extend from cable 70 and connect to a circuit board 52.

The electrical leads 71a and 71b are electrically connected to the circuit board 52 such that when the switch 50 is depressed, a trigger lead 72 carries the first electrical potential from the circuit board 52 to jaw member 110. The second electrical potential is carried by lead 71c directly from the generator (not shown) to jaw member 120 through a terminal connector 150. As best shown in FIG. 1, a switch cap 53 is positioned in electro-mechanical communication with the circuit board 52 along one side of shaft 12b to facilitate activation of switch 50. The position of the switch cap 53 enables the user to easily and selectively energize the jaw members 110 and 120 with a single hand.

The two opposing jaw members 110 and 120 of the end effector assembly 100 are pivotable about pivot assembly 65 from the open position to the closed position for grasping tissue therebetween. Pivot assembly 65 connects through aperture 125 disposed through shaft 12a and aperture 111 disposed through shaft 12b. In this manner, pivot assembly 65 operates to pivotably secure the shafts 12a and 12b during assembly such that the jaw members 110 and 120 are freely pivotable between the open and closed positions.

Figure 5A:
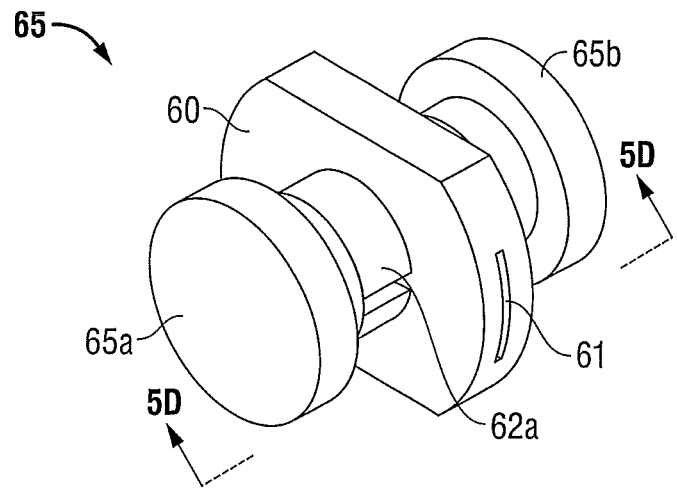
FIG. 5A is an enlarged, left, perspective view of a pivoting hub of FIG. 4.
Figure 5B:
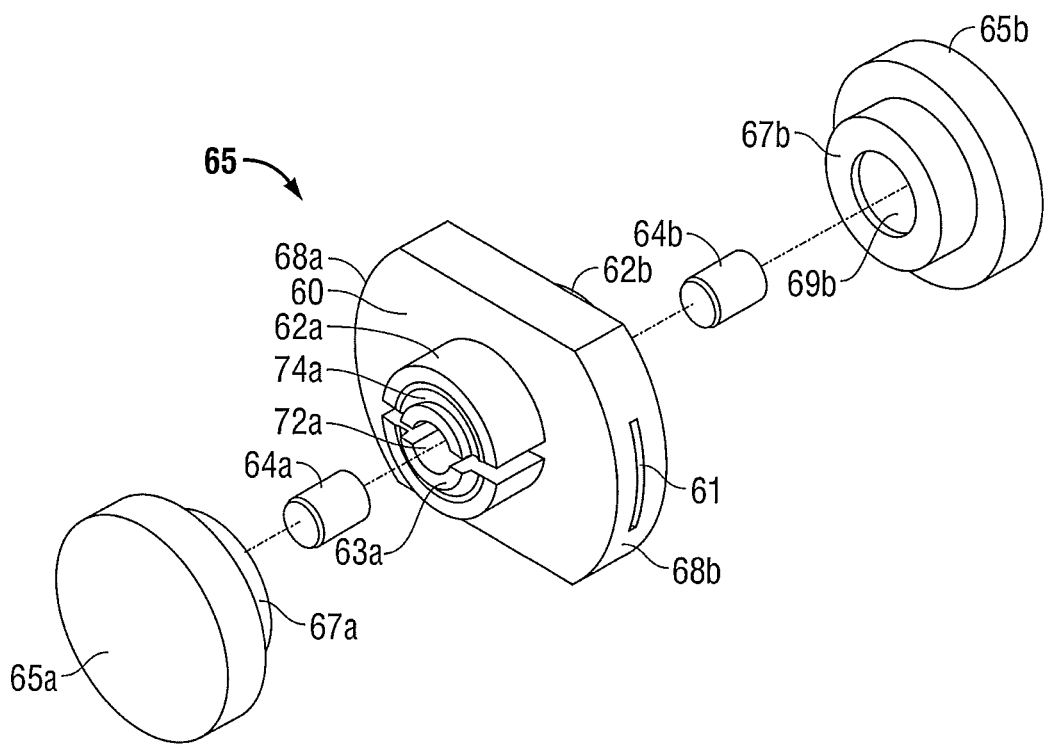
FIG. 5B is a left, perspective view of the pivoting hub of FIG. 5A with parts separated.
Figure 5C:
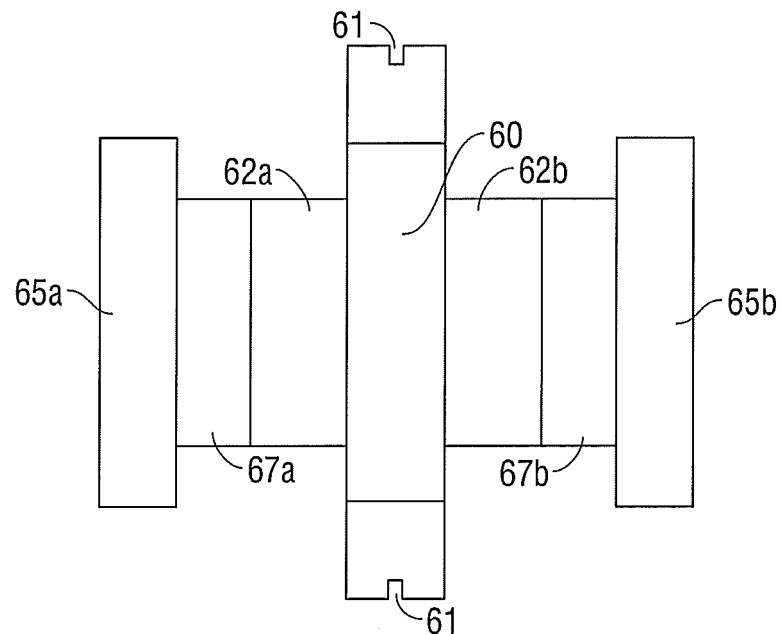
FIG. 5C is an enlarged, top view of the pivoting hub of FIG. 5A.
Figure 5D:
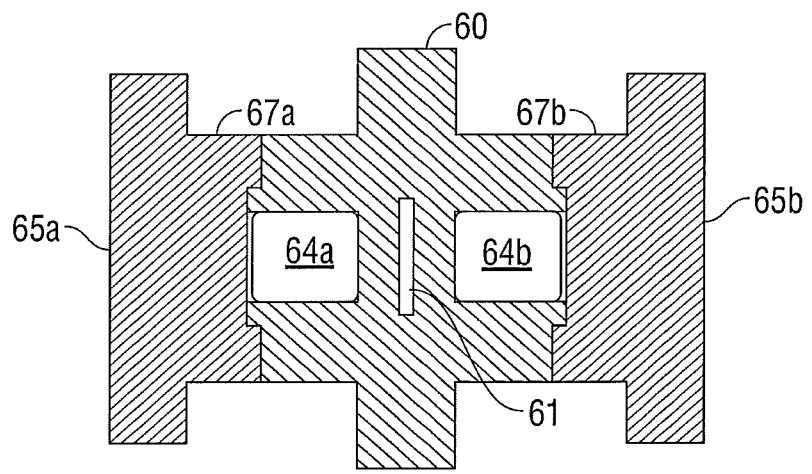
FIG. 5D is a front, cross sectional view of the pivoting hub of FIG. 5A.

As shown in FIGS. 5A-5D, pivot assembly 65 generally includes a hub 60 having a blade slot 61 defined longitudinally therethrough and a pair of shoulders 67a, 67b each having a first end operably coupled to an opposing side of the hub 60. Hub 60 includes a pair of inner protrusions 63a, 63b, that define corresponding inner recesses 72a, 72b, and a pair of outer protrusions 62a, 62b that at least partially surround inner protrusions 63a, 63b, respectively, to define a pair of respective outer recesses 74a, 74b therebetween. Shoulders 67a, 67b include caps 65a, 65b, respectively, defined at a second end thereof. A pair of pivot pins 64a, 64b are configured to be received at one end within recesses 69a, 69b defined in shoulders 67a, 67b, respectively, and at an opposing end within corresponding inner recesses 72a, 72b to matingly engage shoulders 67a, 67b with hub 60. As shown in FIG. 5B, outer recesses 74a, 74b are generally circular in shape and expand a suitable distance between outer protrusions 62a, 62b and inner protrusions 63a, 63b such that upon receiving pivot pins 64a, 64b within inner recesses 72a, 72b, the latitudinal thickness of shoulders 67a, 67b is accommodated within outer recesses 74a, 74b, respectively. In embodiments, pivot pins 64a, 64b are made from steel and hub 60 and caps 65a, 65b are made from an insulative substrate, such as plastic or some other non-conductive material. Alternatively, hub 60 and/or shoulders 67a, 67b may be made from a solid or multi-strand electrically conductive material, e.g., copper/aluminum, which is surrounded by an insulative, non-conductive coating (not shown), e.g., plastic.

Shoulders 67a, 67b and hub 60 may be ultrasonically welded together at one or more weld points. Alternatively, shoulders 67a, 67b and hub 60 may be mechanically engaged in any other suitable fashion, snap-fit, glued, screwed, etc.

Figure 6:
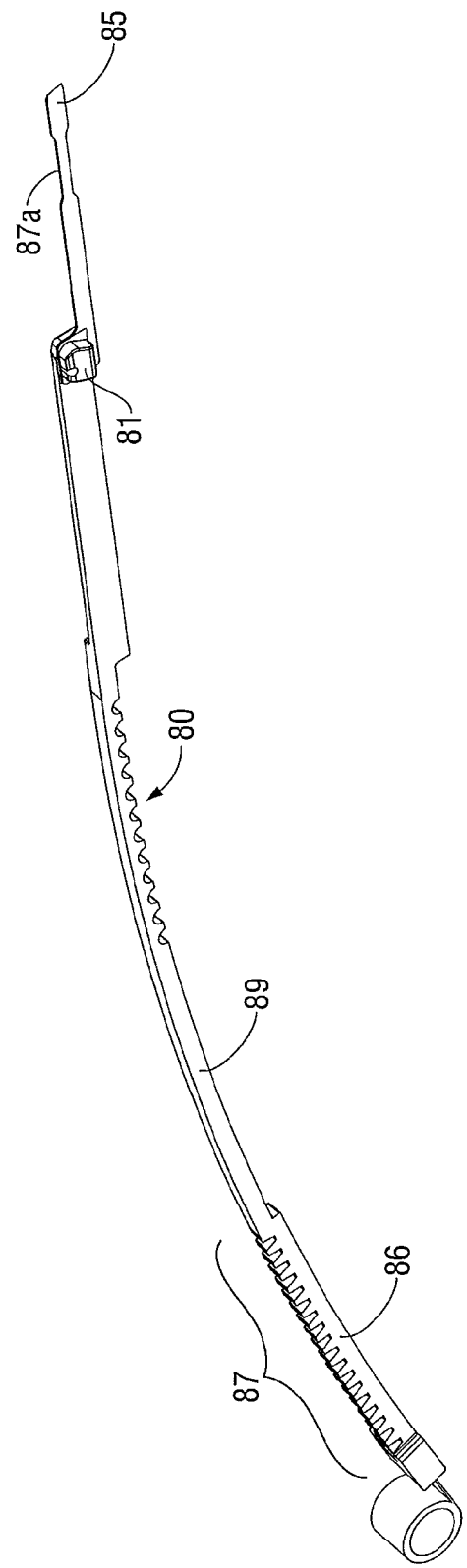
FIG. 6 is an enlarged, perspective view of a cutting mechanism of FIG. 4.
Figure 7:
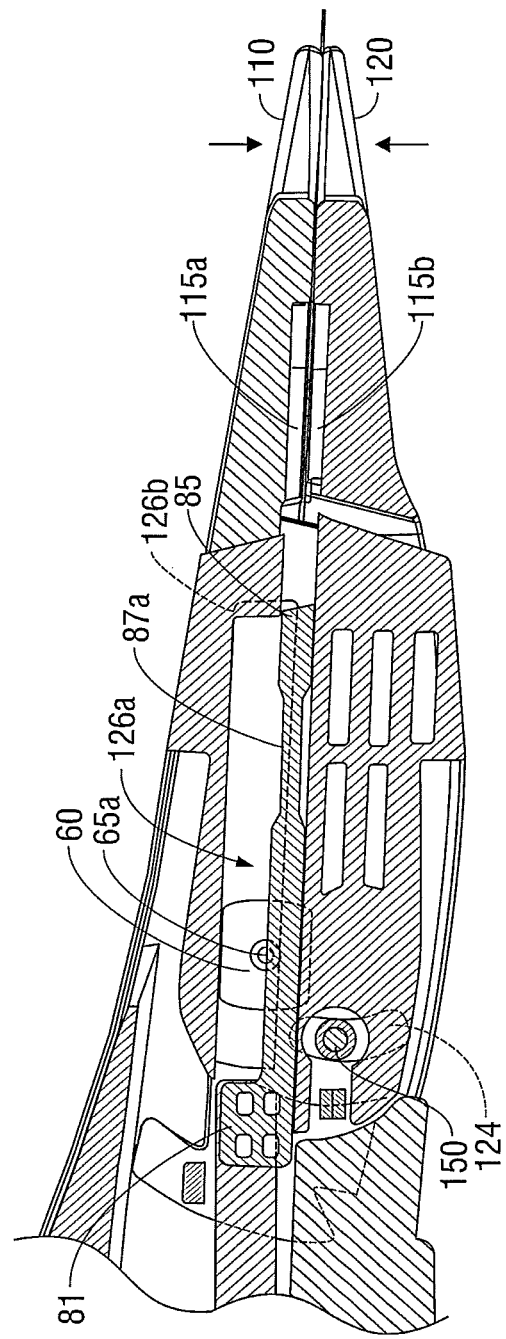
FIG. 7 is an enlarged, side, cross sectional view showing the forceps of FIG. 1 in a closed position and defining a gap distance "G" between opposing jaw members.
Figure 8:
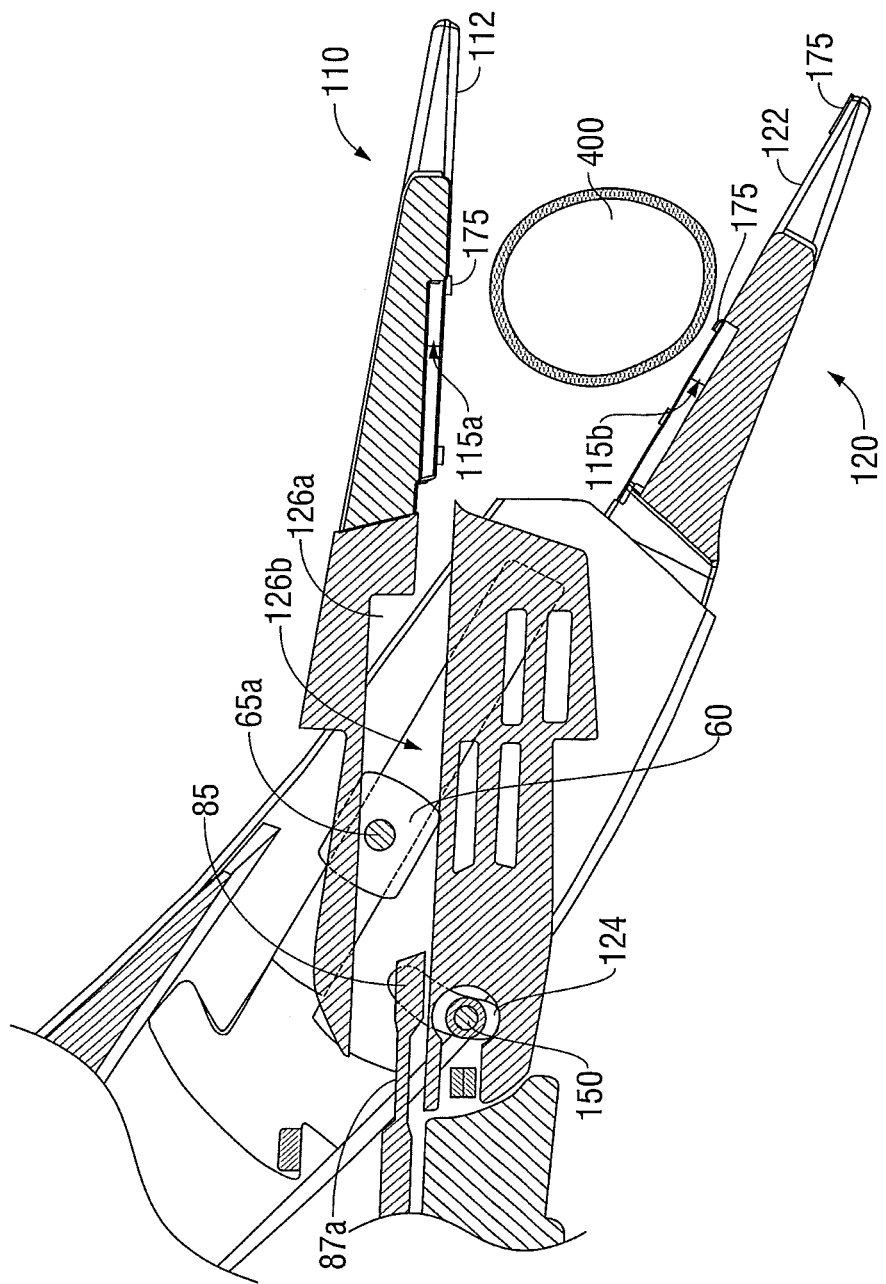
FIG. 8 is an enlarged, side, cross sectional view showing the forceps of FIG. 1 in open configuration for grasping tissue.
Figure 9:
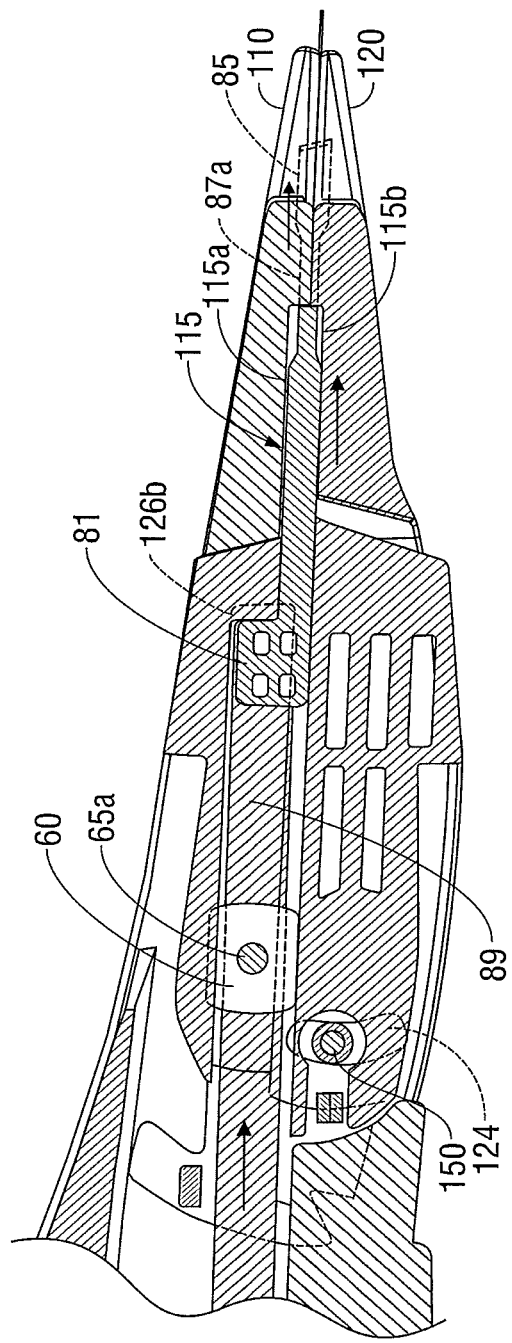
FIG. 9 is an enlarged, side, cross sectional view showing the forceps of FIG. 1 in a closed position and showing the activation and advancement of the cutting mechanism.

As best seen in FIGS. 7-9, the jaw members 110 and 120 include a knife channel 115 disposed therebetween that is configured to allow reciprocation of a cutting mechanism 80 (see FIG. 6) therewithin. One example of a knife channel is disclosed in commonly-owned U.S. Pat. No. 7,267,677. The complete knife channel 115 is formed when two opposing channel halves 115a and 115b associated with respective jaw members 110 and 120 come together upon grasping of the tissue. The complete knife channel 115 aligns with blade slot 61 to permit reciprocation of cutting mechanism 80 therethrough. The knife channel 115 may be tapered or some other configuration, which facilitates or enhances cutting of the tissue during reciprocation of the cutting mechanism 80 in the distal direction (see FIG. 9). Moreover, the knife channel 115 may be formed with one or more safety features that prevent the cutting mechanism 80 from advancing through the tissue until the jaw members 110 and 120 are closed about the tissue. Examples of lockout mechanisms and safety features are described in commonly-owned U.S. Patent Publication No. 2005/0154387 and U.S. Pat. Nos. 7,156,846 and 7,150,097.

Figure 2:
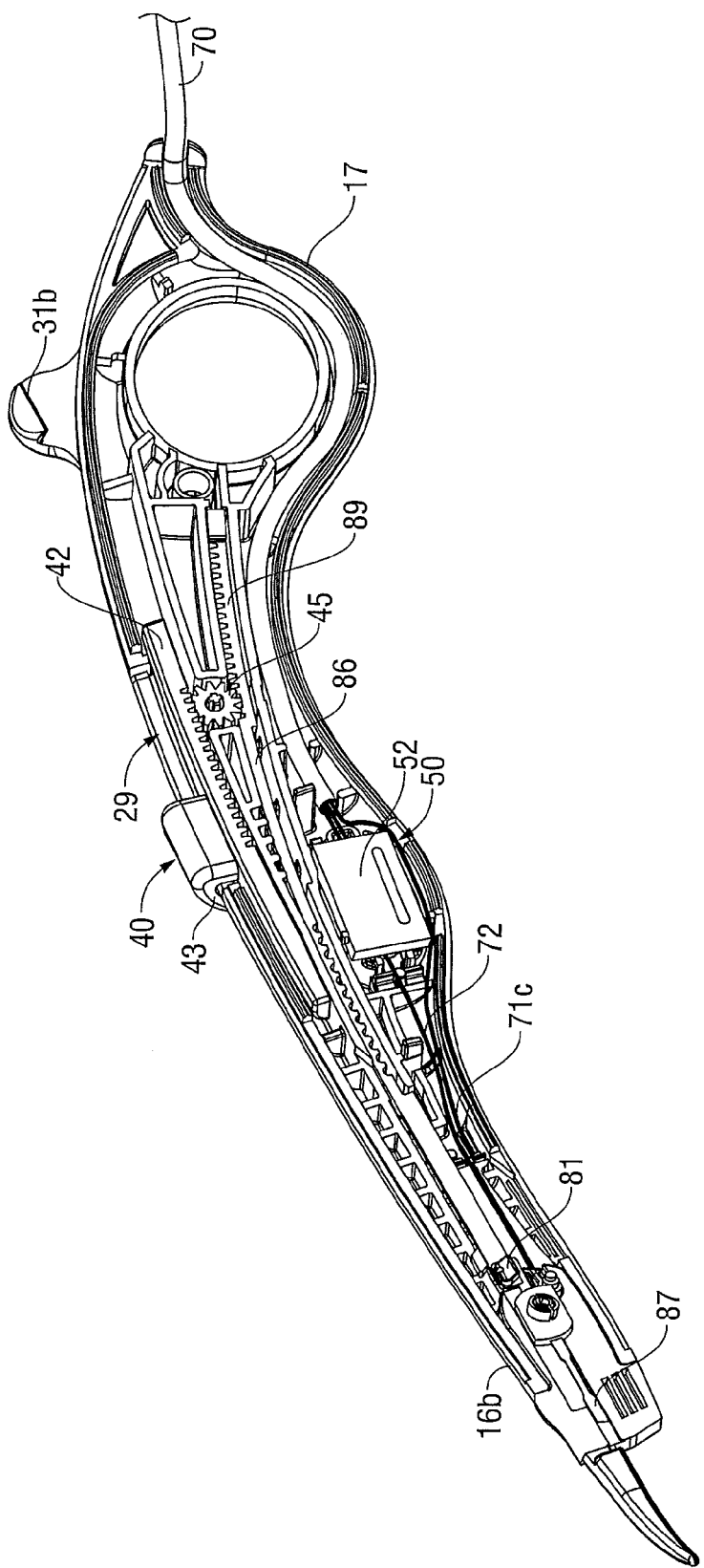
FIG. 2 is an internal, perspective view of the forceps of FIG. 1 showing a rack and pinion actuating mechanism for advancing the cutting mechanism and a series of internally disposed electrical connections for energizing the forceps.
Figure 3:
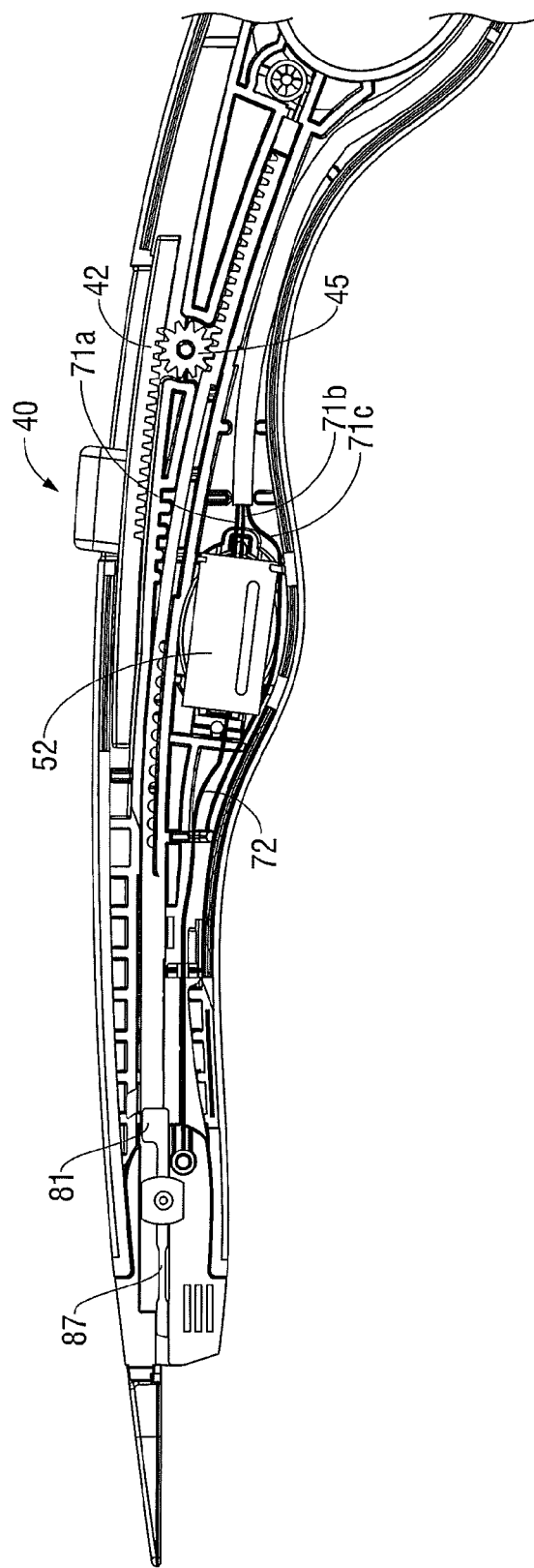
FIG. 3 is an internal, side view of the forceps of FIG. 1 showing the rack and pinion actuating mechanism and the internally disposed electrical connections.

The arrangement of shaft 12b is slightly different from shaft 12a. More particularly, shaft 12b is generally hollow to house the handswitch 50 (and the electrical components associated therewith), an actuating mechanism 40 and the cutting mechanism 80. As best seen in FIGS. 2, 3 and 4, the actuating mechanism 40 includes a rack and pinion system having first and second gear tracks 42 and 86, respectively, and a pinion 45 to advance the cutting mechanism 80. More particularly, the actuating mechanism 40 includes a trigger or finger tab 43 that is operatively associated with a first gear rack 42 such that movement of the trigger or finger tab 43 moves the first rack 42 in a corresponding direction. The actuating mechanism 40 mechanically cooperates with a second gear rack 86, which is operatively associated with a drive rod 89, and which advances the entire cutting mechanism 80, as will be explained in more detail below. Drive rod 89 includes a distal end 81 that is configured to mechanically support the cutting blade 85.

Interdisposed between the first and second gear racks 42 and 86, respectively, is a pinion gear 45 that mechanically meshes with both gear racks 42 and 86 and converts proximal motion of the trigger 43 into distal translation of the drive rod 89 and vice versa. Distal translation of the drive rod 89 advances the blade 85 of the cutting mechanism 80 through tissue 400 grasped between jaw members 110 and 120, i.e., the cutting mechanism 80, e.g., knife, blade, wire, etc., is advanced through blade slot 61 and, subsequently, through channel 115 upon distal translation of the drive rod 89.

The distal end 81 of the cutting mechanism 80 is dimensioned to reciprocate within a channel 126b defined in the proximal end of jaw member 120 when jaw member 110 and 120 are disposed in a closed position (see FIGS. 7 and 9). The proximal portion of jaw member 120 also includes a guide slot 124 defined therethrough that allows a terminal connector 150 or so called "POGO" pin to ride therein upon movement of the jaw members 110 and 120 from the open to closed positions (See FIGS. 7 and 8). The terminal connector 150 is seated within a recess 113. In addition, the proximal end includes an aperture 125 defined therethrough that houses the pivot assembly 65. Jaw member 110 also includes a channel 126a that aligns with channel 126b when the jaw members 110 and 120 are disposed in the closed position about tissue.

As best shown in FIGS. 7 and 8, which show the jaw members 110 and 120 in open and closed orientations, respectively, the operation of the pivoting hub 65 in the capacity as a lockout mechanism is easily described. Pivot assembly 65 is operably coupled with jaw member 120 such that pivoting of jaw member 120 causes identical pivoting movement of pivot assembly 65, i.e., pivot assembly 120 pivots with jaw member 120. In this manner, when jaw members 110 and 120 are moved from the closed position to the open position, hub 60 rotates in translation with jaw member 120 such that blade slot 61 moves out of alignment with knife channel 115 to prevent the cutting mechanism 80 from advancing through hub 60 via blade slot 61. When the jaw members 110 and 120 are moved to the closed position as illustrated in FIG. 9, the hub 60 rotates with jaw member 120 to align blade slot 61 with channels 126a and 126b of jaw members 110 and 120, respectively, to allow distal advancement of cutting mechanism 80 through hub 60 and, subsequently, through knife channel 115. As shown in FIG. 9, the distal end 81 advances through channel 126a and 126b forcing the knife blade 85 through knife channel 115 (115a and 115b) to cut tissue. As described above, when the actuating flange 43 is released, drive rod 89 returns or is biased back to the proximal-most position (not shown) which, in turn, allows the jaw members 110 and 120 to be moved to the open position to release the tissue 400.

Referring now to FIG. 6, blade 85 is flexible so it easily advances through the curved knife channel 115. For example, upon distal advancement of the cutting mechanism 80, the cutting blade 85 will simply flex and ride around the knife channel 115 through the tissue 400 held between jaw members 110 and 120. In one particular embodiment, the blade 85 is flexible and is generally hourglass in configuration and includes a mutually aggregating notch 87a disposed about midway along the blade 85. The mutually aggregating notch 87a reduces the side profile of the blade to facilitate the cutting process. More particularly, the hourglass design of the blade allows the blade 85 to move more easily along the curved knife channel 115 during distal translation thereof.

In some embodiments, one of the jaw members, e.g., 120, includes at least one stop member 175 (see FIG. 8) disposed on the inner facing surface of the electrically conductive sealing surface 122 (and/or 112). The stop member(s) is designed to facilitate gripping and manipulation of tissue and to define a gap "G" between opposing jaw members 110 and 120 during sealing (See FIG. 7). In some embodiments, the separation distance during sealing or the gap distance "G" is within the range of about 0.001 inches (.about.0.03 millimeters) to about 0.006 inches (.about.0.016 millimeters). In some embodiments, a stop member 175 is positioned on either side of the knife channel 115 generally midway along the length of the bottom jaw member 120.

A detailed discussion of these and other envisioned stop members 175 as well as various manufacturing and assembling processes for attaching, disposing, depositing and/or affixing the stop members to the electrically conductive sealing surfaces 112, 122 are described in commonly-assigned, co-pending PCT Application Serial No. PCT/US01/11222.

In operation, the surgeon simply utilizes the two opposing handle members 15 and 17 to grasp tissue between jaw members 110 and 120. The surgeon then activates the handswitch 50 to provide electrosurgical energy to each jaw member 110 and 120 to communicate energy through the tissue held therebetween to effect a tissue seal. Once sealed, the surgeon activates the actuating mechanism 40 to advance the cutting blade 85 through the tissue to sever the tissue 400.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A pivot assembly for use with an open electrosurgical forceps for sealing tissue, comprising:
   a pair of insulative shoulders having a first end defining a cap and a second end operably coupled to opposing sides of an insulative hub, the insulative hub including a knife slot defined therein, wherein the insulative hub is configured to prevent reciprocation of a cutting mechanism through the knife slot in a first configuration and to permit reciprocation of the cutting mechanism through the knife slot in a second configuration, and wherein the knife slot is configured to:
   align with a knife channel when the forceps is disposed in a first configuration to permit advancement of the cutting mechanism from a retracted position proximal to the pivot assembly to an advanced position through the pivot assembly and into tissue grasped by the forceps; and
   misalign with the knife channel when the forceps is disposed in a second configuration to prevent advancement of the cutting mechanism from the retracted position to the advanced position.

2. A pivot assembly according to claim 1, wherein at least one of a pair of jaw members of the forceps is configured to rotate about one of the shoulders.

3. A pivot assembly according to claim 2, wherein rotation of one of the jaw members translates to rotation of the insulative hub between the first and second configurations.

* * * * *